United States Patent
Bao et al.

(10) Patent No.: US 8,460,673 B2
(45) Date of Patent: Jun. 11, 2013

(54) FUSION PROTEIN INHIBITING OSTEOCLAST FORMATION, PREPARATION METHOD AND MEDICINE COMPOSITIONS THEREOF

(75) Inventors: Jun Bao, Shanghai (CN); Haiming Chen, Shanghai (CN); Daocheng Zhu, Shanghai (CN)

(73) Assignee: Shanghai Kexin Biotech Co., Ltd., Shanghai (CN)

( * ) Notice: Subject to any disclaimer, the term of this patent is extended or adjusted under 35 U.S.C. 154(b) by 0 days.

(21) Appl. No.: 13/123,235

(22) PCT Filed: Sep. 29, 2009

(86) PCT No.: PCT/CN2009/074286
§ 371 (c)(1), (2), (4) Date: Jun. 15, 2011

(87) PCT Pub. No.: WO2010/043153
PCT Pub. Date: Apr. 22, 2010

(65) Prior Publication Data
US 2011/0243944 A1  Oct. 6, 2011

(30) Foreign Application Priority Data
Oct. 8, 2008  (CN) .......................... 2008 1 0200865

(51) Int. Cl.
*A61K 39/00* (2006.01)
(52) U.S. Cl.
USPC ..................... 424/185.1; 424/192.1; 514/16.7

(58) Field of Classification Search
None
See application file for complete search history.

(56) References Cited

U.S. PATENT DOCUMENTS
6,419,929 B1 * 7/2002 Anderson .................. 424/192.1

FOREIGN PATENT DOCUMENTS
| CN | 101514232 A | * | 8/2009 |
| JP | 2007231001 A | * | 9/2007 |
| WO | WO 2005085291 A1 | * | 9/2005 |
| WO | PCT/CN2009/074286 | | 1/2010 |

* cited by examiner

*Primary Examiner* — Michael Szperka
(74) *Attorney, Agent, or Firm* — Global IP Services (57) ABSTRACT

The present invention provides a coding gene having the nucleic acid sequence shown as SEQ ID NO:1 and the fusion protein RIG (SEQ ID NO:2) that inhibits osteoclast formation. The present invention also provides the preparation method for the fusion protein RIG as well as synthetic oligonucleotide primers, plasmids and host cells used in the method and a medicine having the above fusion protein RIG as active ingredient. The fusion protein RIG in present invention is derived from humanized immunoglobulin and RANKL with a flexible hinge region. RIG can cross link the cell surface receptor RANK and Fcγ 1 to induce a cytosolic inhibitory signal leading to the inhibition of osteoclast formation. The fusion protein RIG in present invention can play an essential role in treating osteoporosis and bone resorption diseases caused by tumor metastasis.

7 Claims, 4 Drawing Sheets

Control      Binding of RIG to RANKL Receptor

FUSION PROTEIN INHIBITING OSTEOCLAST FORMATION, PREPARATION METHOD AND MEDICINE COMPOSITIONS THEREOF

CROSS REFERENCE TO RELATED PATENT APPLICATION

The present application is the US national stage of PCT/CN2009/074286 filed on Sep. 29, 2009, which claims the priority of the Chinese patent application No. 200810200865.7 filed on Oct. 8, 2008, which application is incorporated herein by reference.

FIELD OF THE INVENTION

The present invention relates to biomedical fields. In particular, the present invention relates to a bio-technique for preparation of a fusion protein. More particularly, the present invention relates to a fusion protein and pharmaceutical compositions that can be used to treat osteoporosis and bone resorption caused by tumor metastasis.

BACKGROUND OF THE INVENTION

Bone formation and bone resorption are two highly related and balanced processes involved in normal bone remodeling. For osteoporosis patients, their osteoclast activity is elevated to such an extent that bone absorption rate exceeds bone formation rate. This process causes bone disease without the loss of bone mineral. Bone is also a frequent target for invasion and metastasis of tumors such as multiple myeloma, mammary cancer, prostatic cancer and lung cancer. During the metastasis process, cancer cells interact with the osteoclast precursors in bone marrow to differentiate into osteoclasts. Consequently, at the bone site for tumor metastasis, the number of osteoclasts is generally observed to increase, and the bone resorption caused by osteoclasts increases as well. In general, excess of osteoclasts, which differentiate from monocytes or macrophages is the major reason for osteoporosis and tumor related bone resorption. Osteoporosis often leads to bone fracture and happens quite often in old people, especially women. In China, according to the 5$^{th}$ population census in 2000, it is anticipated that in 2050 there will be 410 million people of 60 years old or above, about 27.4 percent of the total Chinese population. While the aged population increases rapidly, the susceptible population for osteoporosis quickly increases as well. For example, in the United States, there are 28 million osteoporosis patients, 1.5 million of which had bone fracture (700 thousand vertebra fracture and 250 thousand hipbone fracture). Therefore, WHO and the United Nations named 2000 to 2010 as "The Bone and Joint Decade". According to the information provided by WHO, bone fracture caused by osteoporosis has increased 4 times in recent years, at the same time, bone diseases caused by the higher level osteoclast activity stimulated by tumor metastasis increases constantly. In the United States, bone resorption caused by tumor metastasis has led to about 500 thousand fractures, in which the multiple myeloma, mammary cancer, prostatic cancer and lung cancer are the most frequent sources. However, whether for women having the osteoporosis during menopause or patients having bone resorption caused by tumor metastasis, their diseases are both osteoporoses caused by the excess of osteoclasts. To solve the problem of osteoporosis, scientists all over the world are trying to find a cure to inhibit the excess of osteoclasts. In one case, Pfizer Inc. has submitted their application to the FDA for their new medicine Fablyn. Fablyn, a selective estrogen receptor modulator, is developed to cure osteoporosis of women during menopause by the similar mechanism to that of hormone estrogen. However, the application was declined twice in 2005 and 2006 because there were considerable chances of risk for the patients to have a carcinoma of the endometrium after the treatment. In 2007, Pfizer filed a new application for Fablyn as medicine for osteoporosis with new data. Amgen is also developing a protein medicine named Osteoprotegerin (OPG). OPG can potentially neutralize the activity of RANKL (Receptor Activator for Nuclear Factor KB ligand) to inhibit the excess of osteoclasts. In the meantime, researchers from Institute for Myeloma and Bone Cancer Research in Los Angeles are also working on a peptide that might reduce osteoclast formation: the tumor necrosis factor receptor-associated factor 6 (TRAF6) dominant negative binding peptide (TRAF6dn).

It is well known now that RANKL plays an important role in osteoclast formation. RANKL belongs to the TNF family. Its crystal structure indicates that a special cluster of its molecular structure can bind and activate the osteoclast precursor surface receptor RANK (Receptor Activator for Nuclear Factor κB). RANK is expressed on monocytes, chondrocyte and osteoclast precursor. It is the major receptor for regulation of osteoclast differentiation. RANKL/RANK has been proved the most important signaling pathway for osteoclast formation. During the tumor metastasis RANKL is the major physiological modulator for osteoclast differentiation. RANKL can be secreted directly by tumor cells, thus stimulates the osteoclast differentiation without the help of stromal cell.

Ever since the discovery of RNAKL/RANK signaling pathway, there has been rapid advance on understanding the regulation of osteoclast formation and activation. It has been found that, RANKL binds to the RANK receptor, which in turn phosphorylates ITAM tyrosine to activate DAP12 or FcRγ, as well as the co-activation pathway mediated by coreceptor TREM2 and OSCAR. The phosphorylation of tyrosine kinase ZAP70 and Syk leads to movement of PLCγ and Calcium ion, further activating NFATc1 which enhances osteoclast differentiation.

Osteoclasts are bone resorption cells formed by the fusion of monocyte-macrophage cells. Osteoclast formation requires RANKL and M-CSF co-stimulation as well as ITAM signal. However, human monocyte-macrophage also expresses an IgG inhibiting receptor FcγRIIb, which contains ITIM motif in its cytosolic domain. This receptor belongs to inhibitory receptor superfamily, it upregulates the cytosolic phosphatase SHP-1, while SHP-1 down regulates Syc-BCR to block the PI3K signaling pathway to down regulate ITAM and to inhibit osteoclast formation.

Cross-linking of FcγRIIb and ITAM motif containing receptor can inhibit ITAM's activation on calcium mobility and cell proliferation. Based on the balance of ITAM and ITIM in signaling pathway, the inventors have designed a fusion protein RANKL-Fcγ which can be used to cross link RANK and FcγRIIB receptor to induce ITIM signal thus to inhibit osteoclast formation and bone resorption.

As a cytokine, RANKL binds to the RANKL receptor of monocyte-macrophage cells to activate ITAM (Immunoreceptor tyrosine-based activation motif) signaling pathway. In this pathway, a series of different proteins are phosphorylated, resulting in osteoclast formation through the differentiation of monocyte-macrophages. In the meantime, ITAM signaling pathway is inhibited by ITIM (Immunoreceptor tyrosine-based inhibitory motif). ITIM counteracts ITAM signaling pathway through the activation of SHIP1 (SH2 domain-containing inositol polyphosphate 5' phosphatase) and (SHPT/2) (SH2 domain-containing protein tyrosine phosphatase). In present invention, the inventors used genetic engineering and protein engineering technology to prepare a RANKL-Fcγ fusion protein, RIG, which inhibits the ITAM signaling pathway by activating cytosolic ITIM signaling pathway.

In summary, the first goal of this invention is to provide a DNA coding sequence for the fusion protein RIG that can be used to inhibit osteoclast formation.

The second goal of this invention is to provide fusion protein that can be used to inhibit osteoclast formation.

The third goal of this invention is to provide synthetic oligo-nucleotides used to prepare the above DNA coding sequence.

The fourth goal of this invention is to provide a preparation method for fusion protein RIG.

The fifth goal of this invention is to provide a medicine composition whose active ingredient is fusion protein RIG.

SUMMARY OF THE INVENTION

The present invention provides an isolated nucleic acid sequence having the following 1656 bp sequence (SEQ ID NO:1) that codes the fusion protein RIG that can be used to inhibit osteoclast formation.

```
   1 ATGCGCCGCG CCAGCAGAGA CTACACCAAG TACCTGCGTG GCTCGGAGGA GATGGGCGGC
  61 GGCCCCGGAG CCCCGCACGA GGGCCCCCTG CACGCCCCGC CGCCGCCTGC GCCGCACCAG
 121 CCCCCCGCCG CCTCCCGCTC CATGTTCGTG GCCCTCCTGG GCTGGGGCT GGGCCAGGTT
 181 GTCTGCAGCG TCGCCCTGTT CTTCTATTTC AGAGCGCAGA TGGATCCTAA TAGAATATCA
 241 GAAGATGGCA CTCACTGCAT TTATAGAATT TTGAGACTCC ATGAAAATGC AGATTTTCAA
 301 GACACAACTC TGGAGAGTCA AGATACAAAA TTAATACCTG ATTCATGTAG GAGAATTAAA
 361 CAGGCCTTTC AAGGAGCTGT GCAAAAGGAA TTACAACATA TCGTTGGATC ACAGCACATC
 421 AGAGCAGAGA AAGCGATGGT GGATGGCTCA TGGTTAGATC TGGCCAAGAG GAGCAAGCTT
 481 GAAGCTCAGC CTTTTGCTCA TCTCACTATT AATGCCACCG ACATCCCATC TGGTTCCCAT
 541 AAAGTGAGTC TGTCCTCTTG GTACCATGAT CGGGGTTGGG CCAAGATCTC CAACATGACT
 601 TTTAGCAATG GAAAACTAAT AGTTAATCAG GATGGCTTTT ATTACCTGTA TGCCAACATT
 661 TGCTTTCGAC ATCATGAAAC TTCAGGAGAC CTAGCTACAG AGTATCTTCA ACTAATGGTG
 721 TACGTCACTA AAACCAGCAT CAAAATCCCA AGTTCTCATA CCCTGATGAA AGGAGGAAGC
 781 ACCAAGTATT GGTCAGGGAA TTCTGAATTC CATTTTTATT CCATAAACGT TGGTGGATTT
 841 TTTAAGTTAC GGTCTGGAGA GGAAATCAGC ATCGAGGTCT CCAACCCCTC CTTACTGGAT
 901 CCGGATCAGG ATGCAACATA CTTTGGGGCT TTTAAAGTTC GAGATATAGA TGGATCCGAG
 961 CCCAATATTG TGACAAAACT CACACATGCC CACCGCTGCC CAGCACCTGA ACTCCTGGGG
1021 GGACCGTCAG TCTTCCTCTT CCCCCCAAAA CCCAAGGACA CCCTCATGAT CTCCCGGACC
1081 CCTGAGGTCA CATGCGTGGT GGTGGACGTG AGCCACGAAG ACCCTGAGGT CAAGTTCAAC
1141 TGGTACGTGG ACGGCGTGGA GGTGCATAAT GCCAAGACAA AGCCGCGGGA GGAGCAGTAC
1201 AACAGCACGT ACCGTGTGGT CAGCGTCCTC ACCGTCCTGC ACCAGGACTG GCTGAATGGC
1261 AAGGAGTACA AGTGCAAGGT CTCCAACAAA GCCCTCCCAG CCCCCATCGA GAAAACCATC
1321 TCCAAAGCCA AAGGGCAGCC CCGAGAACCA CAGGTGTACA CCCTGCCCCC ATCCCGGGAT
1381 GAGCTGACCA AGAACCAGGT CAGCCTGACC TGCCTGGTCA AAGGCTTCTA TCCCAGCGAC
1441 ATCGCCGTGG AGTGGGAGAG CAATGGGCAG CCGGAGAACA ACTACAAGAC CACGCCTCCC
1501 GTGCTGGACT CCGACGGCTC CTTCTTCCTC TACAGCAAGC TCACCGTGGA CAAGAGCAGG
1561 TGGCAGCAGG GGAACGTCTT CTCATGCTCC GTGATGCATG AGGCTCTGCA CAACCACTAC
1621 ACGCAGAAGA GCCTCTCCCT GTCTCCGGGT AAATAA
```

The present invention provides a fusion protein RIG having the following amino acid sequence. (SEQ ID NO:2):

```
  1 MRRASRDYTK YLRGSEEMGG GPGAPHEGPL HAPPPPAPHQ PPAASRSMFV ALLGLGLGQV

61 VCSVALFFYF RAQMDPNRIS EDGTHCIYRI LRLHENADFQ DTTLESQDTK LIPDSCRRIK

121 QAFQGAVQKE LQHIVGSQHI RAEKAMVDGS WLDLAKRSKL EAQPFAHLTI NATDIPSGSH

181 KVSLSSWYHD RGWAKISNMT FSNGKLIVNQ DGFYYLYANI CFRHHETSGD LATEYLQLMV

241 YVTKTSIKIP SSHTLMKGGS TKYWSGNSEF HPYSINVGGF FKLRSGEEIS IEVSNPSLLD

301 PDQDATYFGA FKVRDIDGSE PKSCDKTHTC PPCPAPELLG GPSVFLFPPK PKDTLMISRT

361 PEVTCVVVDV SHEDPEVKFN WYVDGVEVHN AKTKPREEQY NSTYRVVSVL TVLHQDWLNG

421 KEYKCKVSNK ALPAPIEKTI SKAKGQPREP QVYTLPPSRD ELTKNQVSLT CLVKGFYPSD

481 IAVEWESNGQ PENNYKTTPP VLDSDGSFFL YSKLTVDKSR WQQGNVFSCS VMHEALHNHY

541 TQKSLSLSPG K
```

Figure 1:
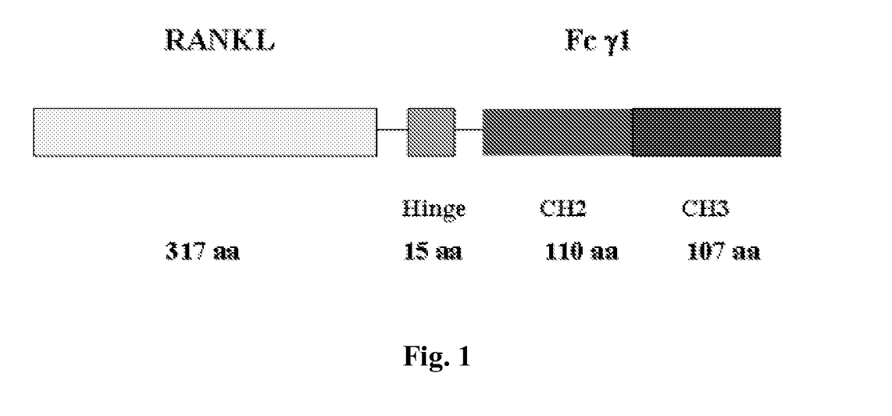
FIG. 1 presents the RIG molecular structure.

RIG is a fusion protein composed of 551 amino acid residues. As illustrated FIG. 1, fusion protein RIG has three regions: region A (RANKL) (Amino acid 1-317), region B (Fc-γ) (Amino acid 335-551) and region C (hinge) (Amino acid 318-334). Region A is derived from human RANKL with the binding site for RANK; region B comes from human IgG having the binding site for IgG receptor FcγRII; region C comes from human immunoglobulin and is a hinge region.

The present invention provides a preparation method for fusion protein RIG comprising: 1) construction of fusion protein RIG coding gene sequence (SEQ ID NO:1); 2) Construction of plasmid pSecTagRIG; 3) Transfection of pSecTagRIG into SP2/0 cell; 4) Positive expression clone selection and screening, RIG protein expression and purification.

The present invention first synthesized the following oligonucleotides as specific primers (SEQ ID NO:3-SEQ ID NO:6):

```
RANKL1 (Sfi I):
5'-GGCCCCGAGGGCCATGCGCCGCGCCAGCAGAGAC-3';

RANKL2 (BamH I):
5'-GGATCCGATCTATATCTCGAACTTTAAAAGC-3';

P3 (Fcg BamH I):
5'-GGATCCGAGCCCAAATCTTGTGAC-3';

P4 (Fcg Not I):
5'-GCGGCCGCTCATTTACCCGGAGACAGGGAGAG-3'.
```

The above primers were used to amplify RANKL and Fcγ using RT-PCR technology. The PCR products were cloned into pCR4-TOPO vector (Invitrogen, CA) accordingly, resulting in plasmids pRANKL and pFcγ). After the sequence verification, RANKL and Fcγ were ligated into expression vector pSecTag to get plasmid pSecTagRIG. This plasmid was transfected into mouse myeloma cell SP2/0, and positive clones with high expression of RIG (having the same amino acid sequence SEQ ID NO:2) were screened. The expression cell lines were grown and expressed RIG protein was purified.

The present invention further provides a pharmaceutical composition that inhibits osteoclast formation, containing a therapeutically effective amount of fusion protein RIG and one or more pharmaceutically acceptable carrier(s).

These carriers include pharmaceutically conventional diluents, excipients, fillers, binders, wetting agents, the disintegrating agents, absorption enhancers, surfactants, absorption carriers, and lubricants. When needed, one may also add flavoring agents and sweetening agents among other items.

The pharmaceutical composition of the invention can be used as injections such as an intravenous injection, transdermal agents such as a hypodermic injection and a patch applied to the skin directly among other methods. It also can be used as a nasal spray and as a throat, mouth, skin, or membrane inhaler. In addition, this pharmaceutical composition can be applied as a nasal aqueous suspension, eye drops, or ear drops. Furthermore, it can be used as a rectal gel, a suppository, and tablets, powder, ball pill, capsule, solution, oil cream, cream, and various other forms. The pharmaceutical composition mentioned above can be prepared, with pharmaceutically conventional methods, to be appropriate dosage forms.

All the pharmaceutical compositions mentioned above generally have a dosage (as the active ingredient RIG) of 0.1-5 mg/kg/week and the treatment course generally lasts 10 to 30 days.

BRIEF DESCRIPTION OF THE DRAWINGS

In the appendix drawings.

PREFERABLE EMBODIMENTS

The following examples are exemplified to further elaborate the invention. It is understood that these examples are only used to illustrate the invention but not to limit the invention in any way. Any changes in the implementation of the invention, by those skilled in the art who is inspired by the description of the invention, are in the scope of the claims attached.

Example 1

Expression of Fusion Protein RIG

Figure 2:
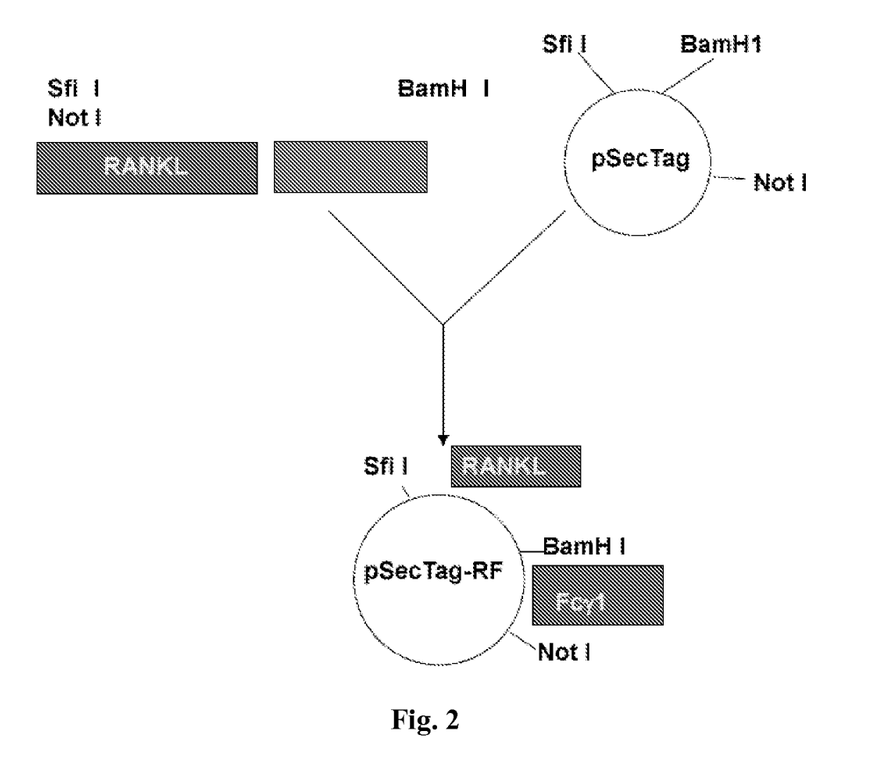
FIG. 2 presents RIG cloning and expression flow chart.

As illustrated in FIG. 2, the expression of the fusion protein includes the following steps: T lymphocytes and B lymphocytes were drawn from circumference blood and purified, from which mRNA were extracted. The specific primers were used to amplify the RANKL and Fcγ genes from T lymphocytes and B lymphocytes respectively using RT-PCR method. The primers used are from:

SEQ ID NO: 3
    5'-GGCCCCGAGGGCCATGCGCCGCGCCAGCAGAGAC-3';

SEQ ID NO: 4
    5'-GGATCCGATCTATATCTCGAACTTTAAAAGC-3';

SEQ ID NO: 5
    5'-GGATCCGAGCCCAAATCTTGTGAC-3';

SEQ ID NO: 6
    5'-GCGGCCGCTCATTTACCCGGAGACAGGGAGAG-3'.

Figure 3:
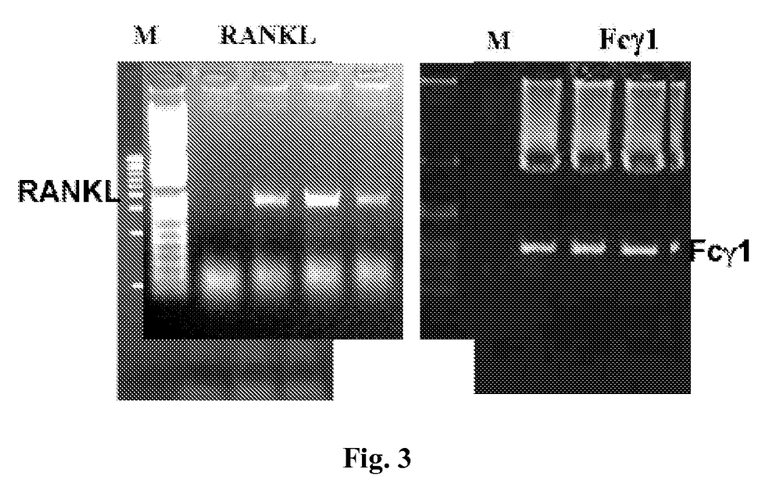
FIG. 3 presents Electrophoresis Analysis of FcγRII and RANKL DNA PCR amplification products.

The amplified RANKL and Fcγ genes were analyzed on 1% agarose electrophoresis. As shown in FIG. 3, the RANKL amplification product is about 970 bp long, while the Fcγ DNA amplification product is about 714 bp long. The two PCR products were cloned separately into CR4-TOPO vector (Invitrogen, CA) to obtain pRANKL and pFcγ plasmids respectively. The recombinant plasmids were sequenced. After the verification of the gene sequences, RANKL and Fcγ genes were double digested with SfiI-BamHI and BamHI-NotI restriction enzymes (NEW ENGLAND BIOLABS) respectively and ligated into the pSecTag expression vector (Invitrogen, CA) double digested with SfiI-BamHI restriction enzymes. The result plasmid pSecTagRIG was sequenced, and the insertion of the DNA is shown to be the same as SEQ ID NO: 1. The plasmid pSecTagRIG was transfected into mouse myeloma SP2/0 cell by regular electroporation, and selected by ZEOCIN resistance. High expression clone for RIG protein (which has amino acid sequence as SEQ ID NO:2) was screened using ELISA method. Briefly, mouse anti human RANKL antibody was coated on ELISA plates, followed by the addition of sample supernatant to be analyzed. At last, enzyme labeled goat anti human IgG antibody was added to test the activity.

The above positive clone, i.e., the mouse myeloma SP2/0 cell containing the plasmid pSecTagRIG, was grown in RPMI1640 medium at 37° C. with 5% CO2 for 15 days. The culture was centrifuged at 2000 rpm and the supernatant was collected. From which the fusion protein RIG was purified using protein A affinity chromatography (GE HealthCare).

Example 2

Binding Experiment of RIG and RANK (RANKL Receptor)

Figure 4:
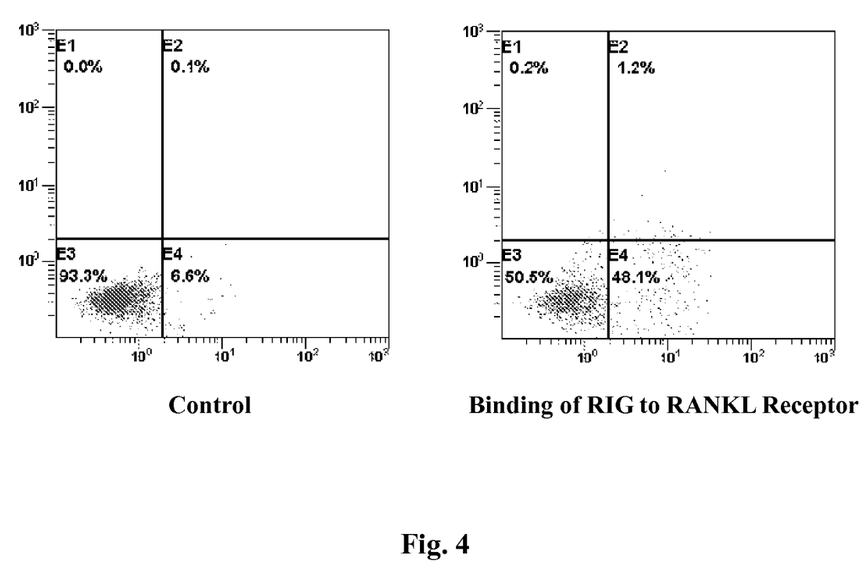
FIG. 4 presents flow analysis of RIG binding ability to RANKL receptor.

$1*10^6$ THP1 monocytes were grown in MCSF and RANKL medium for 72 hours and mixed with 5 μg purified RIG protein from Implementation 1 for additional 1 hour at 4° C. 5 μl FITC labeled anti human RANKL antibody (CALTAG, CA) was then added into the mixture and flow cytometry was used to examine FITC positive cells. As shown in FIG. 4, the result indicates that RIG protein bind to RANK which made the THP1 cell FITC positive. In FIG. 4, SSC-H presents the pellet number in cytoplasm, FSC-H presents the cell size, FL2-H presents PE and FL1-H presents FITC.

Example 3

Figure 5:
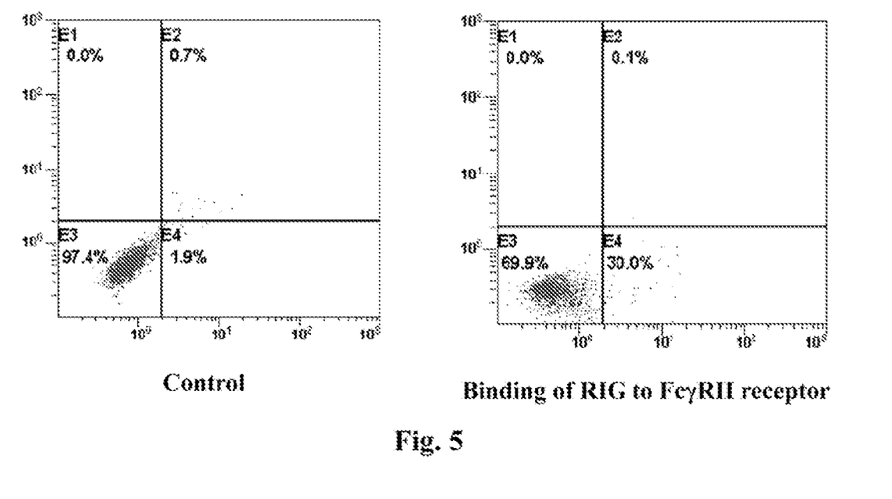
FIG. 5 presents flow analysis of RIG binding ability to FcγRII receptor.
Figure 6:
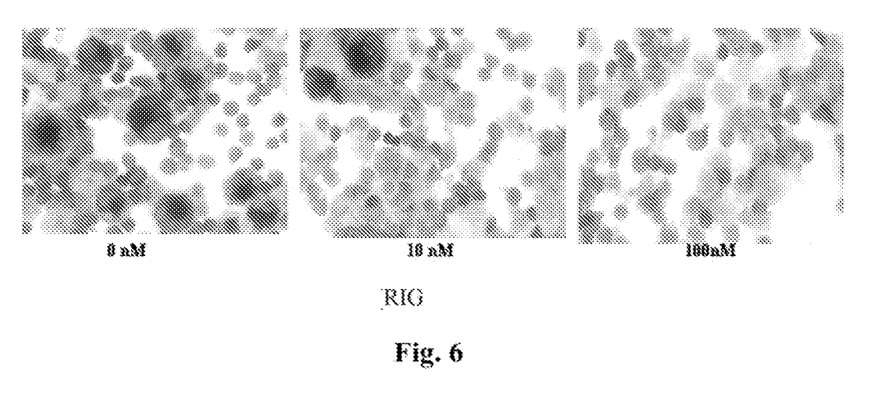
FIG. 6 presents RIG inhibition of osteoclast formation.
Figure 7:
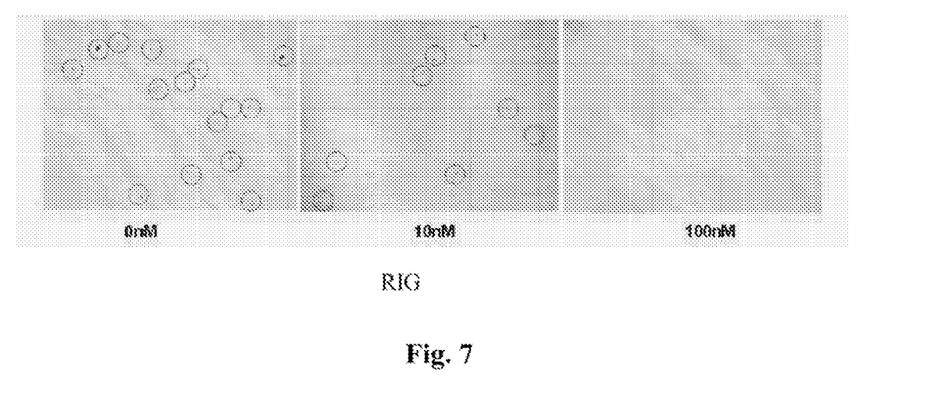
FIG. 7 presents RIG inhibition of the biological activity of osteoclasts.

Binding Experiment of RIG and FcγRII Receptor $1*10^6$ HMC-1 cells were mixed with 5 μg purified RIG protein from Implementation 1 for 1 hour at 4° C. 5 μl FITC labeled anti human IgG antibody (CALTAG, CA) was then added into the mixture and flow cytometry was used to examine FITC positive cells. As shown in FIG. 5, the result indicates that RIG protein can bind to FcγRII receptor which made the HMC-1 cell FITC positive. In FIG. 5, SSC-H presents the pellet number in cytoplasm, FSC-H presents the cell size, FL2-H presents PE and FL1-H presents FITC.

Example 4

Experiment for RIG's Inhibition on Osteoclasts Formation

Anti CD14 microsphere (Miltenyi Biotec, Auburn, Calif.) was used to separate CD14+ cells from the bone marrow or PBMC of multiplemyeloma patients. The cells were then grown in medium containing 50 ng/ml RANKL and 20 ng/ml M-CSF. After three days, the RIG protein and a control sample were added into the medium respectively and the cells were grown for 14 more days. The cells were then harvested and fixed before subjected to TRAP staining analysis using TRAP-staining kit (Sigma, St Louis, Mo.) to check the number of multinucleated osteoclasts. The formation rate of osteoclasts was then evaluated based on the fusion index.

This implantation has shown that RIG can effectively inhibit osteoclast formation at a dose dependant manner.

Example 5

Experiment for RIG's Inhibition on the Biological Activity of Osteoclasts

By analyzing bone resorption of osteoclasts, we further checked the inhibition of RIG on the biological activity of osteoclasts. Briefly, the 150 μm thick mammoth ivory dentine slice with 6 mm diameter was cleaned using sterile water and ultrasound. It was then disinfected in 70% alcohol and illuminated by UV overnight. CD14+ cells were separated from normal human PBMC or bone marrow and grown in MCSF and RANKL medium. $5*104$ CD14+ cells were then stimulated by fusion protein RIG for 21 days on above dentine slices. To check the bone resorption area, the differentiated cells were washed vigorously in distill water first before the slices were dehydrated and blown dry. The slices were then stained using Toluidine blue, and resorption pits were examined by light microscopy and the percentage surface area of lacunar resorption on each dentine slice was measured using an image analysis system.

INDUSTRY APPLICABILITY

The fusion protein RIG in present invention is derived from humanized immunoglobulin and RANKL. Therefore, when delivered into human body as a medicine, the protein does not have any foreign immunogenicity. The flexible C-region (hinge) links RANKL and Fcγ which can induce the cytosolic inhibitory signal and inhibit the RANK-ITAM reaction. The fusion protein RIG in present invention activates cytosolic inhibitory signaling pathway, thus strongly inhibits the osteoclast formation. Consequently, RIG will play an essential role in treating osteoporosis and bone resorption caused by tumor metastasis.

What is claimed is:

1. A fusion protein RIG that inhibits osteoclast formation, having the amino acid sequence of SEQ ID NO:2.

2. The fusion protein RIG of claim 1, wherein the amino acid sequence of SEQ ID NO:2 has a structure with three regions: region A as RANKL, having amino acid residues 1-317 of RIG; region B as Fcγ, having amino acid residues 335-551 of RIG; and region C, being a hinge region.

3. A pharmaceutical composition that inhibits osteoclast formation, containing a therapeutically effective amount of said fusion protein RIG of claim 1 as an active ingredient and one or more pharmaceutically acceptable carrier(s).

4. The fusion protein RIG of claim 2, wherein the region A is derived from human RANKL with a binding site for the RANKL.

5. The fusion protein RIG of claim 2, wherein the region B is derived from human IgG having the binding site for IgG receptor FcγRII.

6. The fusion protein RIG of claim 2, wherein the region C is derived from human immunoglobulin.

7. The fusion protein RIG of claim 2, wherein said fusion protein is encoded by the nucleic acid sequence of SEQ ID NO:1.

* * * * *

SEQUENCE LISTING

<160> NUMBER OF SEQ ID NOS: 6

<210> SEQ ID NO 1
<211> LENGTH: 1656
<212> TYPE: DNA
<213> ORGANISM: Artificial sequence
<220> FEATURE:
<223> OTHER INFORMATION: Synthetic

<400> SEQUENCE: 1

| | | | | | |
|---|---|---|---|---|---|
| atgcgccgcg | ccagcagaga | ctacaccaag | tacctgcgtg | gctcggagga | gatgggcggc | 60 |
| ggccccggag | ccccgcacga | gggccccctg | cacgccccgc | cgccgcctgc | gccgcaccag | 120 |
| ccccccgccg | cctcccgctc | catgttcgtg | gccctcctgg | ggctggggct | gggccaggtt | 180 |
| gtctgcagcg | tcgccctgtt | cttctatttc | agagcgcaga | tggatcctaa | tagaatatca | 240 |
| gaagatggca | ctcactgcat | ttatagaatt | ttgagactcc | atgaaaatgc | agattttcaa | 300 |
| gacacaactc | tggagagtca | agatacaaaa | ttaatacctg | attcatgtag | gagaattaaa | 360 |
| caggcctttc | aaggagctgt | gcaaaaggaa | ttacaacata | tcgttggatc | acagcacatc | 420 |
| agagcagaga | aagcgatggt | ggatggctca | tggttagatc | tggccaagag | gagcaagctt | 480 |
| gaagctcagc | cttttgctca | tctcactatt | aatgccaccg | acatcccatc | tggttcccat | 540 |
| aaagtgagtc | tgtcctcttg | gtaccatgat | cggggttggg | ccaagatctc | caacatgact | 600 |
| tttagcaatg | aaaactaat | agttaatcag | gatggctttt | attacctgta | tgccaacatt | 660 |
| tgctttcgac | atcatgaaac | ttcaggagac | ctagctacag | agtatcttca | actaatggtg | 720 |
| tacgtcacta | aaaccagcat | caaaatccca | agttctcata | ccctgatgaa | aggaggaagc | 780 |
| accaagtatt | ggtcagggaa | ttctgaattc | cattttttatt | ccataaacgt | tggtggattt | 840 |
| tttaagttac | ggtctggaga | ggaaatcagc | atcgaggtct | ccaacccctc | cttactggat | 900 |
| ccggatcagg | atgcaacata | ctttggggct | tttaaagttc | gagatataga | tggatccgag | 960 |
| cccaatattg | tgacaaaact | cacacatgcc | caccgctgcc | cagcacctga | actcctgggg | 1020 |
| ggaccgtcag | tcttcctctt | ccccccaaaa | cccaaggaca | ccctcatgat | ctcccggacc | 1080 |
| cctgaggtca | catgcgtggt | ggtggacgtg | agccacgaag | accctgaggt | caagttcaac | 1140 |
| tggtacgtgg | acggcgtgga | ggtgcataat | gccaagacaa | agccgcggga | ggagcagtac | 1200 |
| aacagcacgt | accgtgtggt | cagcgtcctc | accgtcctgc | accaggactg | gctgaatggc | 1260 |
| aaggagtaca | agtgcaaggt | ctccaacaaa | gccctcccag | cccccatcga | gaaaaccatc | 1320 |
| tccaaagcca | aagggcagcc | ccgagaacca | caggtgtaca | ccctgccccc | atcccgggat | 1380 |
| gagctgacca | agaaccaggt | cagcctgacc | tgcctggtca | aaggcttcta | tcccagcgac | 1440 |
| atcgccgtgg | agtgggagag | caatgggcag | ccggagaaca | actacaagac | cacgcctccc | 1500 |
| gtgctggact | ccgacggctc | cttcttcctc | tacagcaagc | tcaccgtgga | caagagcagg | 1560 |
| tggcagcagg | ggaacgtctt | ctcatgctcc | gtgatgcatg | aggctctgca | caaccactac | 1620 |
| acgcagaaga | gcctctccct | gtctccgggt | aaataa | | | 1656 |

<210> SEQ ID NO 2
<211> LENGTH: 551
<212> TYPE: PRT
<213> ORGANISM: Artificial sequence
<220> FEATURE:
<223> OTHER INFORMATION: Synthetic

<400> SEQUENCE: 2

-continued

```
Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
                100                 105                 110

Pro Asp Ser Cys Arg Arg Ile Lys Gln Ala Phe Gln Gly Ala Val Gln
            115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
                180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
    275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp Gly Ser Glu
305                 310                 315                 320

Pro Lys Ser Cys Asp Lys Thr His Thr Cys Pro Pro Cys Pro Ala Pro
                325                 330                 335

Glu Leu Leu Gly Gly Pro Ser Val Phe Leu Phe Pro Pro Lys Pro Lys
            340                 345                 350

Asp Thr Leu Met Ile Ser Ala Thr Pro Glu Val Thr Cys Val Val Val
        355                 360                 365

Asp Val Ser His Glu Asp Pro Glu Val Lys Phe Met Trp Tyr Val Asp
    370                 375                 380

Gly Val Glu Val His Asn Ala Lys Thr Lys Pro Ala Glu Glu Gln Tyr
385                 390                 395                 400

Asn Ser Thr Tyr Ala Val Val Ser Val Leu Thr Val Leu His Gln Asp
                405                 410                 415

Trp Leu Asn Gly Lys Glu Tyr Lys Cys Lys Val Ser Asn Lys Ala Leu
            420                 425                 430
```

```
Pro Ala Pro Ile Glu Lys Thr Ile Ser Lys Ala Lys Gly Gln Pro Ala
            435                 440                 445

Glu Pro Gln Val Tyr Thr Leu Pro Pro Ser Arg Asp Glu Leu Thr Tyr
    450                 455                 460

Asn Gln Val Ser Leu Thr Cys Leu Val Lys Gly Phe Tyr Pro Ser Asp
465                 470                 475                 480

Ile Ala Val Glu Trp Glu Ser Asn Gly Gln Pro Glu Asn Asn Tyr Lys
                485                 490                 495

Thr Thr Pro Pro Val Leu Asp Ser Asp Gly Ser Phe Phe Leu Tyr Ser
            500                 505                 510

Lys Leu Thr Val Asp Lys Ser Arg Trp Gln Gln Gly Asn Val Phe Ser
            515                 520                 525

Cys Ser Val Met His Glu Ala Leu His Asn His Tyr Thr Gln Lys Ser
            530                 535                 540

Leu Ser Leu Ser Pro Gly Lys
545                 550

<210> SEQ ID NO 3
<211> LENGTH: 34
<212> TYPE: DNA
<213> ORGANISM: Artificial sequence
<220> FEATURE:
<223> OTHER INFORMATION: Synthetic

<400> SEQUENCE: 3
ggccccgagg gccatgcgcc gcgccagcag agac                              34

<210> SEQ ID NO 4
<211> LENGTH: 31
<212> TYPE: DNA
<213> ORGANISM: Artificial sequence
<220> FEATURE:
<223> OTHER INFORMATION: Synthetic

<400> SEQUENCE: 4
ggatccgatc tatatctcga actttaaaag c                                 31

<210> SEQ ID NO 5
<211> LENGTH: 24
<212> TYPE: DNA
<213> ORGANISM: Artificial sequence
<220> FEATURE:
<223> OTHER INFORMATION: Synthetic

<400> SEQUENCE: 5
ggatccgagc ccaaatcttg tgac                                         24

<210> SEQ ID NO 6
<211> LENGTH: 32
<212> TYPE: DNA
<213> ORGANISM: Artificial sequence
<220> FEATURE:
<223> OTHER INFORMATION: Synthetic

<400> SEQUENCE: 6
gcggccgctc atttacccgg agacagggag ag                                32
```